United States Patent [19]
Bonnet

[11] Patent Number: 5,509,892
[45] Date of Patent: Apr. 23, 1996

[54] ENDOSCOPIC INSTRUMENT

[75] Inventor: Ludwig Bonnet, Knittlingen, Germany

[73] Assignee: Richard Wolf GmbH, Knittlingen, Germany

[21] Appl. No.: 251,770

[22] Filed: May 31, 1994

[30] Foreign Application Priority Data

Nov. 30, 1993 [DE] Germany .......................... 93 18 282.1

[51] Int. Cl.$^6$ ..................................... A61B 1/00
[52] U.S. Cl. ...................... 600/156; 600/153; 600/157; 600/135; 600/129
[58] Field of Search .................. 128/4, 6, 7; 604/31, 604/33; 606/46; 600/101, 105, 106, 135, 130, 129, 157, 153, 156

[56] References Cited

U.S. PATENT DOCUMENTS

| | | | |
|---|---|---|---|
| 3,835,842 | 9/1974 | Iglesias | 128/7 |
| 3,850,162 | 11/1974 | Iglesias | 128/6 |
| 3,850,175 | 11/1974 | Iglesias | 128/303 |
| 4,630,598 | 12/1986 | Bonnet | 128/7 |
| 4,920,961 | 5/1990 | Grossi et al. | 606/14 |

FOREIGN PATENT DOCUMENTS

| | | | |
|---|---|---|---|
| 1067174 | 10/1959 | Germany | 128/7 |
| 7817368 | 9/1978 | Germany . | |

OTHER PUBLICATIONS

Richard Wolf GmbH, Continuous Irrigation Resectoscopes With 25° or 5° Telescopes, Nov. 1989, p. D28.
Richard Wolf GmbH, Continuous Irrigation Resectoscope With Telescope 25°, Active, Nov. 1989, p. D31.
Richard Wolf GmbH, Instruments For Urology, Autumn 1979.

*Primary Examiner*—Richard J. Apley
*Assistant Examiner*—Beverly M. Flanagan
*Attorney, Agent, or Firm*—Panitch Schwarze Jacobs & Nadel

[57] ABSTRACT

An endoscopic instrument, particularly a continuous flushing cysto-urethroscope, has an oval cross-sectioned outer shaft and an inner shaft having a contour formed by two semi-circular arcs with different diameters, the arcs having their openings facing each other and connected by two approximately straight sides. The inner shaft is so dimensioned that it contacts the inside of the outer shaft at three points in a linear manner along essentially the entire shaft length, thus forming three free spaces between the inner shaft and the outer shaft for conveying rinsing or flushing fluids. The free spaces may be closed off at their distal ends with flanges projecting from the outer surface of the inner shaft. Passageways formed within the inner shaft between its walls and examination optics and a treatment instrument, which may be inserted in the inner shaft, serve as additional channels for conveying the fluids, while circumferentially and axially spaced groups of apertures near the distal end region of the outer shaft allow passage of fluids between the treatment site and the free spaces which convey the fluids.

11 Claims, 2 Drawing Sheets

ENDOSCOPIC INSTRUMENT

FIELD OF THE INVENTION

The invention concerns an endoscopic instrument, specifically a continuous flushing cysto-urethroscope.

BACKGROUND OF THE INVENTION

These kinds of instruments are known and afford minimally invasive treatment of, for example, adenomas or tumors of the prostate. The actual treatment proceeds by means of a special treatment instrument within the instrument itself, for example by a laser-, HF- or microwave-probe. This allows the treatment to be observed through examination optics, namely an endoscope. To ensure a clear view, it is expedient to develop the instrument as a suction-flushing instrument, so that liquid flushing agent is pumped in front of the viewing area of the distal endoscope window, and the liquid is then removed via openings through the instrument.

Because particles such as mucous membrane parts, blood coagulum and the like should be drawn off together with the flushing agent, it is necessary that the suction canal(s) be of at least sufficiently large dimensions for the liquids to flow back. Moreover, the cross-section of the draining canal must correspond to the cross-section of the supply canal or could even be slightly bigger, in order to avoid in any case an excess pressure through bubbles. These demands, however, conflict with the demands for a small caliber instrumentation.

From DE-GM 84 16 392 a uretero-renoscope is known having an oval outer shaft and a smaller inner shaft forming an empty space in between for the draining off of liquids. To be sure, because of its oval outer shaft, this instrument already ensures a comparatively large and very usable inner cross-section while having a small perimeter. However, the cross-sections of the canals for supplying and draining of the flushing agent are rather small. It is also felt to be disadvantageous that, upon insertion of a laser probe, this can only be introduced insufficiently in the area of the laser fiber. A reduction of the shaft cross-section in this area, however, would make it impossible to introduce the probe head, which has a larger diameter than the remaining part of the probe. Finally, the instrument's structure makes it difficult to clean.

To be sure, there are already known some resectoscopes that are more easily cleaned. However, many feature a plurality of instrument parts, generally three separable parts, and have therefore proven to be difficult to handle.

SUMMARY OF THE INVENTION

In view of the aforementioned problems, it is an object of the invention to develop an endoscopic instrument of the above type that avoids the above-mentioned disadvantages while producing a slim and easy to handle instrument, which enables safe handling with the smallest possible caliber of the instrument.

According to the invention, an endoscopic instrument, particularly a continuously flushing cysto-urethroscope, has an outer shaft with an oval cross-sectioned outer contour and an inner shaft guided within the outer shaft, such that the cross-sectional contour of the inner shaft deviates from that of the outer shaft to form at least one free space between the shafts for conveying a flushing or rinsing fluid, such as water. The inner shaft also provides a passageway for the insertion of examination optics and a treatment instrument, and the space between the optics and instrument, on one hand, and the inner wall of the inner shaft, on the other hand, provide an additional canal or canals for conveying fluids.

The oval cross-sectioned outer contour of the shaft ensures a good use of the shaft cross-section with comparatively little strain when inserted. An inner shaft in the form of a pipe is installed in this outer shaft, wherein the pipe contour is formed from two semi-circular arcs, open towards one another and of differing diameters, connected by two approximately straight sides. The peculiar form of the inner shaft is so dimensioned that the inner shaft (in the cross-section) touches the outer shaft at three points. That is, it has linear contact with the outer shaft and is thus designed to be fixed, within it. Because of the linear contact, only slight friction is to be expected when the inner shaft is inserted into the outer shaft.

Simultaneously, three canals are formed between the inner and outer shafts, these canals being closed off at their distal ends by flanges on the inner shaft, and merging at their proximal ends with the suction connection of the instrument. The direction of flow of the flushing agent from its emergence at the distal end of the inner shaft is directed from there by means of corresponding apertures in the outer shaft near the distal end. In this way the following is ensured: the still-clean flushing agent first emerges in the region of the distal window of the endoscope optics, flows towards the area of treatment, and finally turns around so that it is then taken up at the outer side of the outer shaft and carried away.

The specific cross-sectional form of the inner shaft not only has special advantages regarding the canal formation, but also uses the space in a special way for arranging the examination optics and the treatment instrument, when the space is so dimensioned that its inner diameter in the region of the larger semi-circular arc of its outer contour corresponds to the outer diameter of the examination optics and in the region of the smaller semi-circular arc of its outer contour corresponds to the diameter of the treatment instrument. Then, the treatment instrument and the examination optics are safely guided within the shaft, whereby the shaft width between the semi-circular arcs is preferably so dimensioned that the examination optics and the treatment instrument touch each other.

This special advantage becomes especially obvious if a laser probe is inserted as the treatment instrument, and this probe has, in comparison with the instrument shaft (laser fiber), a thicker head which must first be guided through the instrument for emergence at the distal end. With the previously described inner shaft contour, it is possible to insert this laser head into the inner shaft only when the examination optics has not yet been inserted, so that the nominally greater width, which would be required for insertion and guiding of the head, will now be available. After the laser head has passed the distal end, the examination optics are inserted, which then assures that the laser fiber is axially movable while being completely inserted inside of the inner shaft. In comparison to known instruments of this type, this makes possible a considerably more precise and reliable steering of the laser probe. Moreover, the shaft cross section is put to optimal use. The remaining space serves as flushing canals.

As is usual with instruments of this type, the instrument terminates distally in a channel-shaped part, which preferably stretches over both the outer shaft and the inner shaft. A particularly advantageous construction results when a reinforcement is provided in this channel-shaped part on the inner side of the outer shaft. The reinforcement projects slightly inwardly over the remaining inner contour of the shaft and against which a flange of the inner shaft frictionally impinges. Because of this projection to the inside, the flange, and with it the inner shaft, is lightly tensioned with respect to the outer shaft and consequently ensures a firm and defined fit of the inner shaft in the outer shaft. Because this inner projection is only provided in the last distal end region of the outer shaft, the inner shaft and outer shaft can be formed in such a way that they slide in one another with slight play and are assembled and disassembled without great exertion of force. Only at the end of the insertion process must an increased force be overcome, which at the same time signals to the operator the correct seating in the assembly process.

Preferably, the apertures in the outer shaft are arranged in groups, so that sieve-like openings with a large total suction cross-section result, and so that a danger of injury from sucking the walls of body cavities against them can be excluded. To ensure an even flow of liquid around the entire outer shaft, it is advantageous to arrange the groups of apertures spread out at 120 degree intervals around the circumference.

In addition to spreading the groups of apertures around the circumference, it is also especially advantageous to arrange them at varying distances in the axial direction of the shaft. According to the invention, a group of apertures is provided in the channel-shaped part and the two other groups are provided in the lower region of the closed part of the outer shaft. This has the advantage that a reliable suction is still ensured, even when a portion of the apertures is covered, for example when working in the region of the sphincter muscle.

Finally, a further advantageous embodiment of the invention is achieved when the instrument is constructed essentially in two parts, namely comprising the outer shaft with suction connection as well as a coupling at the proximal end plus the inner shaft with corresponding coupling counterpart as well as a flushing connection, an insertion connection for the instrument as well as a connection for the insertion and fixing of the examination optics, which usually also includes the examination optics itself. This makes possible an easily handled instrument, with only two parts to harmonize, disassemble, and assemble, and which is especially advantageous for cleaning.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF PREFERRED EMBODIMENT

Figure 1:
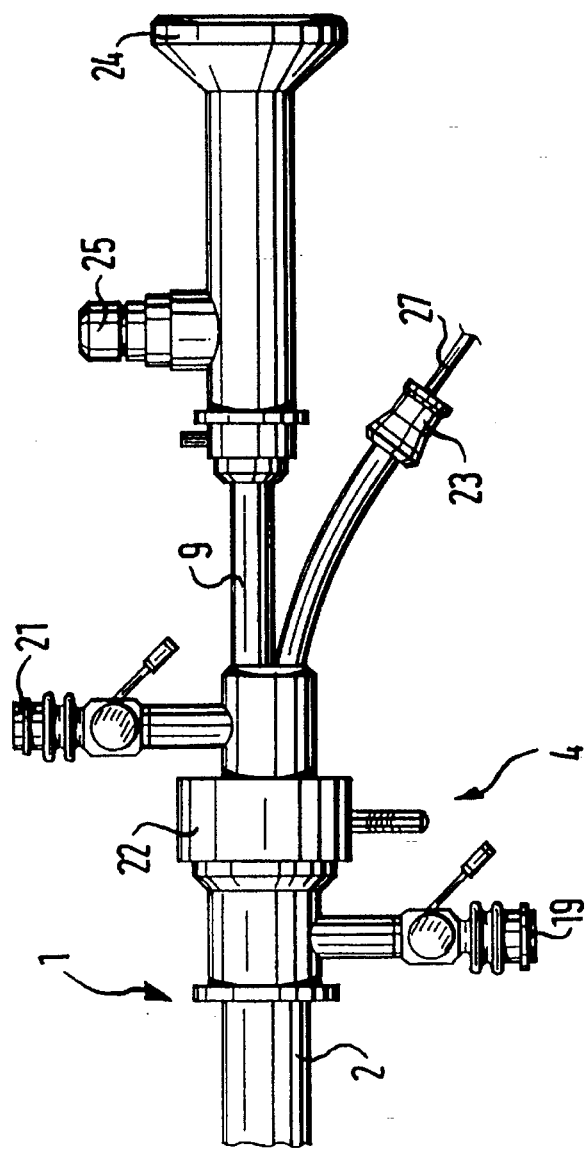
FIG. 1 is a schematic representation of a side view of the instrument according to the invention with the distal end slightly enlarged and broken away.
Figure 1:
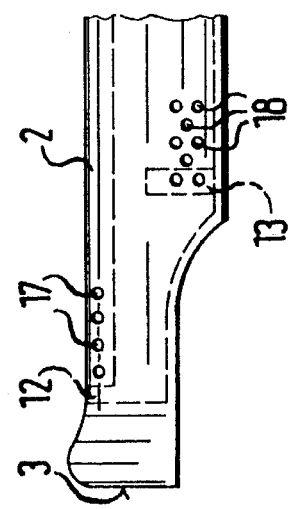

The schematically represented endoscopic instrument in FIG. 1 shows a continuous flushing cysto-urethroscope 1.

Figure 3:
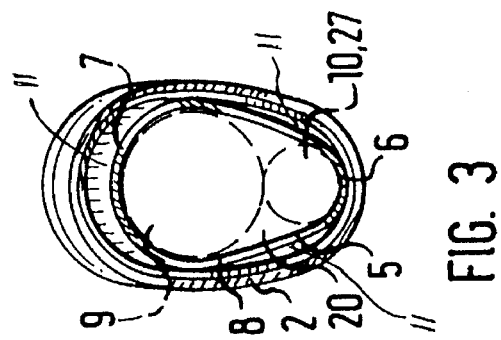
FIG. 3 is a front view of the instrument in the direction of the arrow in FIG. 2 but without examination optics and without a treatment instrument.

This instrument 1 features an outer shaft 2 that stretches from the distal end 3 of the instrument to a proximal connection part 4, and is formed by an oval cross-sectioned pipe, as shown in FIG. 3.

Within the outer shaft 2 an inner shaft 5 is installed, which stretches nearly to the distal end 3 of the instrument on one end and to the proximal connection part 4 on the other. This inner shaft 5 has the cross-sectional contour seen in FIG. 3 and is also formed of a pipe. This pipe 5 consists in cross-section of a small semi-circular arc 6 (in FIG. 3 at the bottom) and a larger semi-circular arc 7 (in FIG. 3 on top), with their openings facing each other and connected via the straight-lined sides 8 to form the continuous pipe cross-section seen in FIG. 3. The inner diameter of the large semi-circular arc 7 is so dimensioned to correspond to the outer diameter of the endoscope 9 which is to be inserted into it, while the diameter of the small semi-circular arc 6 is so dimensioned to correspond to the diameter of a treatment instrument 10. In FIG. 3, the objects 9 and 10 are only suggested by broken-line circles. The length of the sides 8 is chosen so that objects 9 and 10 can be guided within the shaft 5 in a defined manner, although being axially shiftable. In other words, in the ideal case, the endoscope 9 and the treatment instrument 10 have linear contact in the region of the inner shaft 5.

The inner shaft 5 is so dimensioned and so positioned within the outer shaft 2 that a linear contact results between shafts 2 and 5 at the points where the large semi-circular arc 7 merges with the sides 8 and at the mid-point of the small semi-circular arc 6 (see FIG. 3). The arrangement is thus characterized by the following: a clear distance remains in the area between the outer side of the larger semi-circular arc 7 and the inner side of the outer shaft 2 so that a total of three canals 11 is formed between the inner shaft 5 and the outer shaft.

Figure 2:
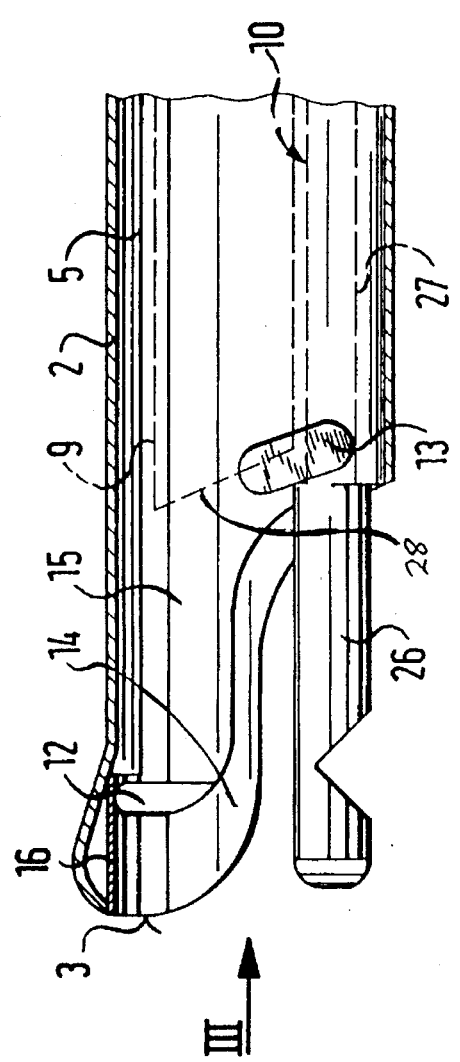
FIG. 2 is an enlarged representation of a side view of the distal end of the instrument with the outer shaft shown in the longitudinal section.

At the distal end these canals 11 are closed off by corresponding flanges 12 and 13 projecting on the outside near the distal end of the inner shaft 5. These flanges 12 and 13 are arranged at an offset of 120° corresponding to the arrangement of the canals 11, whereby the flanges 13, arranged as a pair, still lie within the fully enclosed shaft part, while the flange 12 lies in the region in which the outer shaft 2 runs out in a channel-shaped end-region 14 and the inner shaft 5 runs out in a channel-shaped end-region 15. The flange 12 is positioned at the distal end of the channel-shaped end-region 15 and fits snugly (through elastic formation of the inner shaft 5 in the distal area) against an inner reinforcement 16 of the Channel-shaped end-region 14. As FIG. 2 shows, the pipe of the outer shaft 2 in the channel-shaped end-region 14 is widened in the form of a head-shaped shaped bulge and strengthened on the inside by pipe segment 16 which is soldered in. In this way, in spite of the widening of the inner contour a certain narrowing occurs against which the flange 12 is supported. The flanges 12 and 13 are represented in FIG. 1, greatly simplified.

The outer shaft 2 features a group of apertures 17 in the area of the shaft's channel-shaped end-region 14 that form the entrance openings of one of the canals 11. Proximally offset therefrom, two additional groups of apertures 18 are provided in the outer shaft, around the region of flanges 13.. These form the entrance openings to the remaining canals 11. These canals 11 terminate in the proximal connection part 4 in a ring-canal (not shown), which is provided as a connection to a source of sub-atmospheric pressure via a closeable connection 19.

The canal 20, formed in the inner shaft 5 between endoscope 9 and the treatment instrument 10, is connected at its proximal end to a flushing-connection 21. This canal 20 terminates at its distal end approximately where the fully enclosed part of the shaft 5 merges into the channel-shaped end-region 15. Exactly here, however, also lies the distal viewing window 28 of the endoscope 9 (as shown in FIG. 2). The flushing agent, arriving through the flushing connection 21 in the instrument, therefore flows through the canal 20, over the viewing window 28 of the endoscope 9, and into the body cavity and the treatment area, which is situated about where arrow III is shown in FIG. 2. The flushing agent flows around the distal end of the instrument and via the apertures 17 and 18, which are on the outerside of shaft 2, flows into the canals 11 from where it is conducted to the suction connection 19.

The instrument 1 has, in the region of the proximal connection part 4, a coupling 22, which is located between the suction connection 19 and the flushing connection 21. After loosening this coupling, the inner shaft 5 can be pulled out of the outer shaft 2, in which case, after overcoming the increased friction between the flange 12 and the inner reinforcement 16, the inner shaft 5 can be effortlessly pulled out of the outer shaft 2 because it is guided therein with play. In the opposite manner, during assembly, increased resistance will be noticeable only shortly before the insertion is complete. After overcoming this resistance, the instrument will be properly assembled.

On the proximal side of the flushing connection 21, an instrument connection 23 is provided, which is likewise closeable and in which a laser probe (in the embodiment according to FIG. 1) is inserted as the treatment instrument 10. Also on the proximal side of the flushing connection 21, an opening for the insertion of the endoscope 9 is provided. The ocular of the endoscope 9 (in FIG. 1) is designated 24 and the light guide connection for the supply of the illuminating optics is designated 25.

As shown in FIG. 2, where a laser probe is inserted as a treatment instrument 10, the head 26 of the laser probe is clearly thicker than the laser fiber 27 because of the prism located within it. However, the inner contour of the inner shaft 5 in the lower area of the small semi-circular arc 6, is adapted not to the head, 26, but to the laser fiber 27, so that the head 26 can only be inserted through the inner shaft 5 if the examination optics 9 is removed. In this way, the circumference of the instrument 1, on one hand, can be kept especially small, and on the other hand, an especially good and safe guiding of the laser probe can be ensured.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

I claim:

1. An endoscopic instrument (1) with proximal and distal ends, comprising an outer shaft (2) with an oval cross-sectional contour and an inner shaft (5) guided on the inside of the outer shaft, said inner shaft having a cross-sectional outer contour differing from the inside of the outer shaft so as to form a free space (11) between them for conveying fluids, said inner shaft (5) being provided near its distal end (3) with outwardly projecting flanges (12, 13) which close off the free space (11) formed between the inner shaft (5) and the outer shaft (2) for conveying fluids, said inner shaft having a further canal (20) for conveying fluids and having a passageway for examination optics (9) and for a treatment instrument (10), wherein the cross-sectional contour of the inner shaft is formed of two semi-circular arcs (6,7) with different diameters, with their openings facing each other, and connected by two approximately straight sides (8), and wherein the inner shaft is so dimensioned that its outer contour contacts the inside of the outer shaft at three points in a linear manner along essentially the entire shaft length.

2. An endoscopic instrument according to claim 1, wherein a distal end region of the outer shaft (2) has apertures (17, 18) for passing fluids, said apertures lying proximally of said flanges (12, 13).

3. An endoscopic instrument according to claim 1, wherein the further canal (20) for conveying fluids is formed between the inner shaft (5) and examination optics (9) and treatment instrument (10) which may be inserted in said inner shaft.

4. An endoscopic instrument according to claim 2, wherein the apertures (17, 18) on the outer shaft (2) are arranged in groups distributed at approximately 120 degree intervals around the circumference.

5. An endoscopic instrument according to claim 4, wherein the groups of apertures (17,18) are arranged at axially differing distances along the outer shaft (2), and a group of apertures (17) is provided in a channel-shaped part (14) near the distal end of the outer shaft (2).

6. An endoscopic instrument according to claim 1, essentially constructed in two parts, one part comprising the outer shaft (2) with a suction connection (19) and a coupling (22) at the proximal end, and the other part comprising the inner shaft (5) with a coupling counter-part (22), flushing connection (21), insertion connection (23) for the treatment instrument, and a connection for inserting and fixing the examination optics (9).

7. An endoscopic instrument according to claim 1, wherein the instrument is a continuously flushing cysto-urethroscope.

8. An endoscopic instrument (1) with proximal and distal ends, comprising an outer shaft (2) with an oval cross-sectional contour and an inner shaft (5) guided on the inside of the outer shaft, said inner shaft having a cross-sectional outer contour differing from the inside of the outer shaft so as to form a free space (11) between them for conveying fluids, wherein the inner shaft (5) fits snugly against the outer shaft (2) where the larger (7) of the semi-circular arcs (6,7) merges into the sides (8) and at the middle of the smaller semi-circular arc (6), said inner shaft having a further canal (20) for conveying fluids and having a passageway for examination optics (9) and for a treatment instrument (10), wherein the cross-sectional contour of the inner shaft is formed of two semi-circular arcs (6,7) with different diameters, with their openings facing each other, and connected by two approximately straight sides (8), and wherein the inner shaft is so dimensioned that its outer contour contacts the inside of the outer shaft at three points in a linear manner along essentially the entire shaft length.

9. An endoscopic instrument (1) with proximal and distal ends, comprising an outer shaft (2) with an oval cross-sectional contour and an inner shaft (5) guided on the inside of the outer shaft, said inner shaft having a cross-sectional outer contour differing from the inside of the outer shaft so as to form a free space (11) between them for conveying fluids, said inner shaft having a further canal (20) for conveying fluids and having a passageway for examination optics (9) and for a treatment instrument (10), wherein the cross-sectional contour of the inner shaft is formed of two semi-circular arcs (6,7) with different diameters, with their openings facing each other, and connected by two approximately straight sides (8), and wherein the inner shaft (5) is so dimensioned that wherein the inner shaft is so dimensional that its outer contour contacts the inside of the outer shaft at three points in a linear manner along essentially the entire shaft length and the inner diameter of the inner shaft (5) in the region of the larger semi-circular arc (7) corresponds to the outer diameter of the examination optics (9) and in the region of the smaller semi-circular arc (6) corresponds to the outer diameter of a treatment instrument (27).

10. An endoscopic instrument (1) with proximal and distal ends, comprising an outer shaft (2) with an oval cross-sectional contour and an inner shaft (5) guided on the inside of the outer shaft, said inner shaft having a cross-sectional outer contour differing from the inside of the outer shaft so as to form a free space (11) between them for conveying fluids, said inner shaft having a further canal (20) for conveying fluids and having a passageway for examination optics (9) and for a treatment instrument (10), wherein the cross-sectional contour of the inner shaft is formed of two semi-circular arcs (6,7) with different diameters, with their openings facing each other, and connected by two approximately straight sides (8), and wherein the inner shaft is so dimensioned that its outer contour contacts the inside of the outer shaft at three points in a linear manner along essentially the entire shaft length, wherein the inner shaft (5) and the outer shaft (2) each terminate at their respective distal ends in a channel-shaped part (14, 15) and wherein outer shaft (2) in the distal end-region of the channel-shaped part (14) is provided with a reinforcement which projects slightly inwardly over the final distal inner contour of the outer shaft and is frictionally engaged by a flange (12) projecting from the inner shaft (5).

11. An endoscopic instrument (1) with proximal and distal ends, comprising an outer shaft (2) with an oval cross-sectional contour and an inner shaft (5) guided on the inside of the outer shaft, said inner shaft having a cross-sectional outer contour differing from the inside of the outer shaft so as to form a free space (11) between them for conveying fluids, said inner shaft having a further canal (20) for conveying fluids and having a passageway for examination optics (9) and for a treatment instrument (10) comprising a laser probe, wherein the cross-sectional contour of the inner shaft is formed of two semi-circular arcs (6,7) with different diameters, with their openings facing each other, and connected by two approximately straight sides (8), and wherein the inner shaft is so dimensioned that its outer contour contacts the inside of the outer shaft at three points in a linear manner along essentially the entire shaft length.

* * * * *